United States Patent
Hsu et al.

(10) Patent No.: US 12,377,239 B2
(45) Date of Patent: Aug. 5, 2025

(54) RESPIRATORY DEVICE FOR PROVIDING BUBBLE CPAP

(71) Applicant: Fisher & Paykel Healthcare Limited, Auckland (NZ)

(72) Inventors: Peter Chi-Yang Hsu, Auckland (NZ); Simei Gomes Wysoski, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 860 days.

(21) Appl. No.: 17/593,353

(22) PCT Filed: Mar. 20, 2020

(86) PCT No.: PCT/IB2020/052566
§ 371 (c)(1),
(2) Date: Sep. 16, 2021

(87) PCT Pub. No.: WO2020/188526
PCT Pub. Date: Sep. 24, 2020

(65) Prior Publication Data
US 2022/0168536 A1    Jun. 2, 2022

Related U.S. Application Data

(60) Provisional application No. 62/821,587, filed on Mar. 21, 2019.

(51) Int. Cl.
*A61M 16/14* (2006.01)
*A61M 16/00* (2006.01)
(Continued)

(52) U.S. Cl.
CPC ........ *A61M 16/14* (2013.01); *A61M 16/0003* (2014.02); *A61M 16/0051* (2013.01);
(Continued)

(58) Field of Classification Search
CPC .......... A61M 16/0003; A61M 16/0066; A61M 16/14; A61M 16/16
See application file for complete search history.

(56) References Cited

U.S. PATENT DOCUMENTS

| 3,724,454 A | 4/1973 | Brown |
| 3,806,102 A | 4/1974 | Valenta et al. |

(Continued)

FOREIGN PATENT DOCUMENTS

| EP | 777507 B1 | 6/1997 |
| EP | 1287843 A2 | 3/2003 |

(Continued)

OTHER PUBLICATIONS

International Search Report in corresponding International Patent Application No. PCT/IB/2020/052566, dated Jul. 1, 2020, in 6 pages.

(Continued)

*Primary Examiner* — Kathryn E Ditmer
(74) *Attorney, Agent, or Firm* — Knobbe Martens Olson & Bear LLP

(57) ABSTRACT

Respiratory systems with a flow generator can provide bubble CPAP therapy by controlling the pressure of a flow of gas delivered to a patient. The controller of the respiratory system can control a motor speed of its flow generator so as to control the pressure of the flow of gas. The controller can also detect presence of bubbling and/or possible leaks in the gas pathway of the system. The respiratory system can include a high flow respiratory system.

18 Claims, 9 Drawing Sheets

(51) Int. Cl.
  *A61M 16/10* (2006.01)
  *A61M 16/16* (2006.01)
  *A61M 16/20* (2006.01)
(52) U.S. Cl.
  CPC .... *A61M 16/0066* (2013.01); *A61M 16/1005* (2014.02); *A61M 16/16* (2013.01); *A61M 16/209* (2014.02); *A61M 2016/0027* (2013.01); *A61M 2205/15* (2013.01); *A61M 2205/3334* (2013.01); *A61M 2205/3365* (2013.01); *A61M 2205/8206* (2013.01)

(56) References Cited

U.S. PATENT DOCUMENTS

| | | | |
|---|---|---|---|
| 4,192,836 | A | 3/1980 | Bartscher et al. |
| 5,943,473 | A | 8/1999 | Levine |
| 6,805,120 | B1 | 10/2004 | Jeffrey et al. |
| 7,044,129 | B1 | 5/2006 | Truschel et al. |
| 7,305,987 | B2 | 12/2007 | Scholller et al. |
| D657,368 | S | 4/2012 | Magee et al. |
| D667,838 | S | 9/2012 | Magee et al. |
| 8,439,031 | B1 | 5/2013 | Rothermel et al. |
| D739,427 | S | 9/2015 | Jung et al. |
| D761,863 | S | 7/2016 | Debitsch et al. |
| D772,252 | S | 11/2016 | Myers et al. |
| D806,717 | S | 1/2018 | Bae et al. |
| 10,016,169 | B2 | 7/2018 | Meador et al. |
| D831,059 | S | 10/2018 | Bao |
| D835,657 | S | 12/2018 | Anzures et al. |
| D835,666 | S | 12/2018 | Saleh et al. |
| D835,667 | S | 12/2018 | Saleh et al. |
| 10,226,200 | B2 | 3/2019 | Vassallo et al. |
| D846,583 | S | 4/2019 | Martin et al. |
| 10,314,990 | B2 | 6/2019 | Richards-Kortum et al. |
| 10,342,950 | B2 | 7/2019 | Bath et al. |
| D885,410 | S | 5/2020 | Butler |
| D887,441 | S | 6/2020 | Lorca Norambuena |
| D892,141 | S | 8/2020 | Clifford et al. |
| D892,142 | S | 8/2020 | Clifford et al. |
| D892,832 | S | 8/2020 | Onuma |
| D892,833 | S | 8/2020 | Onuma |
| D893,547 | S | 8/2020 | Dumas et al. |
| 10,864,343 | B2 | 12/2020 | Bath et al. |
| D913,304 | S | 3/2021 | VanDuyn et al. |
| D914,039 | S | 3/2021 | Zimmerman et al. |
| D914,726 | S | 3/2021 | Gouliard et al. |
| D916,721 | S | 4/2021 | Kirkeby |
| D916,743 | S | 4/2021 | Sim et al. |
| D916,878 | S | 4/2021 | Kim et al. |
| D918,224 | S | 5/2021 | Velamuri et al. |
| D922,405 | S | 6/2021 | Norman |
| 11,039,797 | B2 | 6/2021 | Meador et al. |
| D928,190 | S | 8/2021 | Hartman et al. |
| D928,813 | S | 8/2021 | Nurutdinov et al. |
| D940,729 | S | 1/2022 | Campbell et al. |
| 12,048,810 | B2 | 7/2024 | Dennis et al. |
| 2003/0029451 | A1 | 2/2003 | Blair et al. |
| 2003/0047185 | A1* | 3/2003 | Olsen ................ A61M 16/0841 128/203.22 |
| 2004/0244804 | A1 | 12/2004 | Olsen et al. |
| 2005/0150494 | A1 | 7/2005 | DeVries et al. |
| 2006/0174882 | A1 | 8/2006 | Jagger et al. |
| 2010/0078024 | A1 | 4/2010 | Andrieux et al. |
| 2011/0308518 | A1 | 12/2011 | McGroary et al. |
| 2012/0260718 | A1 | 10/2012 | Sparks et al. |
| 2013/0228180 | A1 | 9/2013 | Ahmad et al. |
| 2014/0014110 | A1 | 1/2014 | Adams |
| 2014/0277914 | A1 | 9/2014 | Fish et al. |
| 2015/0083123 | A1* | 3/2015 | Tero ................ A61M 16/0003 128/205.25 |
| 2015/0186023 | A1 | 7/2015 | Alisanski et al. |
| 2015/0258291 | A1* | 9/2015 | Richards-Kortum ........................ A61M 16/0066 128/205.25 |
| 2017/0224234 | A1* | 8/2017 | Ahlmen ............. A61M 16/024 |
| 2017/0304570 | A1* | 10/2017 | Landis ............. A61M 16/0051 |
| 2018/0015245 | A1 | 1/2018 | Frame et al. |
| 2018/0071469 | A1 | 3/2018 | Oldfield et al. |
| 2018/0110948 | A1 | 4/2018 | Dellaca et al. |
| 2018/0140927 | A1 | 5/2018 | Kito et al. |
| 2019/0167937 | A1* | 6/2019 | Sims ................ A61M 16/0858 |
| 2019/0184128 | A1 | 6/2019 | Lucio |
| 2021/0023318 | A1* | 1/2021 | Tatum ................ A61M 16/024 |
| 2021/0181932 | A1 | 6/2021 | Han et al. |
| 2022/0347423 | A1 | 11/2022 | Babbage et al. |
| 2024/0024602 | A1 | 1/2024 | Peiris et al. |

FOREIGN PATENT DOCUMENTS

| | | | | |
|---|---|---|---|---|
| EP | 2123321 | A1 | 11/2009 | |
| EP | 1061981 | B1 | 9/2010 | |
| EP | 2644220 | A1 | 10/2013 | |
| WO | WO 2005/063323 | A1 | 7/2005 | |
| WO | WO 2010/033429 | A1 | 3/2010 | |
| WO | WO 2013/067509 | A1 | 5/2013 | |
| WO | WO2013/148901 | A1 | 10/2013 | |
| WO | WO 2013/154439 | A1 | 10/2013 | |
| WO | WO 2014/085431 | A1 | 6/2014 | |
| WO | WO 2015/165845 | A1 | 11/2015 | |
| WO | WO 2016/133406 | A1 | 8/2016 | |
| WO | WO-2017126980 | A2 * | 7/2017 | ........ A61M 16/0069 |
| WO | WO 2018/033863 | | 2/2018 | |
| WO | WO-2018042355 | A1 * | 3/2018 | ........ A61M 16/0051 |
| WO | WO 2019/193535 | A1 | 10/2019 | |
| WO | WO 2019/245391 | A1 | 12/2019 | |
| WO | WO 2020/188526 | A1 | 9/2020 | |
| WO | WO 2021/046537 | A1 | 3/2021 | |
| WO | WO 2021/049953 | A1 | 3/2021 | |
| WO | WO 2022/058982 | A1 | 3/2022 | |

OTHER PUBLICATIONS

Written Opinion in corresponding International Patent Application No. PCT/IB/2020/052566, dated Jul. 1, 2020, in 9 pages.
International Preliminary Report on Patentability in corresponding International Patent Application No. PCT/IB/2020/052566, dated Sep. 16, 2021, in 10 pages.

* cited by examiner

RESPIRATORY DEVICE FOR PROVIDING BUBBLE CPAP

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE DISCLOSURE

The present disclosure relates to methods and systems for providing a respiratory flow therapy to a patient. In particular, the present disclosure relates to using a flow generator to provide bubble CPAP therapy.

BACKGROUND

Breathing assistance apparatuses are used in various environments such as hospital, medical facility, residential care, or home environments to deliver a flow of gases to users or patients. A breathing assistance or respiratory therapy apparatus (collectively, "respiratory apparatus" or "respiratory devices") may be used to deliver supplementary oxygen or other gases with a flow of gases, and/or a humidification apparatus to deliver heated and humidified gases. A respiratory apparatus may allow adjustment and control over characteristics of the gases flow, including flow rate, temperature, gases concentration, humidity, pressure, etc. Sensors, such as flow sensors and/or pressure sensors, are used to measure characteristics of the gases flow.

SUMMARY

Bubble Continuous Positive Airway Pressure (CPAP) is a form of respiratory therapy in which a patient (typically an infant) is supplied with a flow of gas via a patient interface. The flow of gas is typically provided by a gas source in the wall of a hospital or clinic, or may be provided by cylinders of compressed air and/or oxygen, for example during transport. The patient interface is connected to two conduits, which are an inspiratory conduit and an expiratory conduit. The inspiratory conduit provides gas to the patient. The expiratory conduit provides a passage for exhaled gases from the patient. The expiratory conduit is in communication with a pressure regulator, which is used to set pressure. The pressure regulator may be a chamber with a column of water into which an end portion of the expiratory conduit is submerged. The exhaled gases are discharged into the pressure regulator. The exhaled gases being discharged into the water results in bubbling of the water i.e. a bubbling effect. The patient interface is typically configured to form a seal with the patient's mouth and/or nose. Examples of sealed patient interfaces can include a nasal mask, an oral mask, a full face mask, nasal pillows, or a cannula with sealing nasal prongs.

In some locations, such as in certain developing countries or in a remote area, a wall source may not be available. The present disclosure provides systems and methods of providing bubble CPAP therapy with a flow generator alternative to and/or optionally in addition to a wall source. The flow generator can also include an integrated humidifier to heat and humidify the flow of gas. An example of a flow generator with an integrated humidifier is a high flow respiratory apparatus. A heated breathing tube can also be used with the high flow respiratory apparatus to deliver the flow of gas from the humidifier to the patient interface. The flow generator can also include an integrated blender to provide supplementary gases to the gases flow. The flow generator is preferably a flow generator that draws in ambient gases e.g. ambient air rather than be connected to a gases source e.g. a gas tank or a wall source. The blender allows a supplementary gas or gases to be mixed with the drawn in ambient gases.

The high flow respiratory apparatus can provide various modes of therapy, including but not limited to high flow therapy (also known as a nasal high flow therapy, or tracheal high flow therapy), CPAP, bi-level, and bubble CPAP, so that the patient need not switch to a different respiratory apparatus when switching to a different mode of respiratory therapy (for example, when the patient's condition changes).

The high flow respiratory apparatus is capable of operating in a bubble CPAP therapy mode, or a nasal high flow therapy mode (as described in more detail below). Additionally or alternatively the high flow respiratory apparatus may also be capable of operating in other high flow therapy modes e.g. tracheal high flow or other high flow. Nasal high flow is delivered through a nasal interface. Tracheal high flow can be delivered by a tracheal interface. Other interfaces may also be possible e.g. an oral interface to provide high flow to the airways via the oral passage. The described respiratory device can operate in high flow therapy mode or bubble CPAP mode.

The high flow respiratory apparatus device operates as a flow controlled device, as described in more detail below (for example the high flow respiratory apparatus may control motor of the blower to achieve a target flow.) The target flow may be a constant flow rate. The target flow may be set by a user, or be based on the device being in a bubble CPAP therapy mode or a nasal high flow therapy mode. In one example the controller may include predefined target flow rates for bubble CPAP therapy mode and nasal high flow therapy mode. The predefined target flow rates may be stored within a memory of the controller.

When operating in the bubble CPAP mode, the high flow respiratory apparatus can control a motor speed of its flow generator, which can be a blower, in order to deliver a constant flow rate (including substantially constant flow rate). The apparatus can monitor the pressure in the breathing circuit (also referred to as the breathing tube or the inspiratory conduit) or in the flow path of the apparatus, and can adjust the target motor speed if the pressure exceeds this limit. The apparatus can also replace the pressure relief valve in a conventional bubble CPAP system with software control to provide better pressure control in the flow of gas. The apparatus can provide a plurality of alarms and monitoring. For example, the apparatus can determine if there is an irregular amount of leak, an occlusion, intermittent bubbling, a suggested and/or automatic flow rate change, the flow rate not meeting an inspiratory demand if the pressure exceeds a threshold, and/or detect whether or not there is bubbling. The high flow respiratory apparatus further can also limit the pressure generated such that pressure delivered to the patient is below a pressure limit. In one example in bubble CPAP mode the flow rate may be a high flow rate.

The term respiratory apparatus and respiratory device can be interchangeably used to described and define the same item.

The respiratory apparatus or respiratory device may be part of a respiratory system comprising one or more additional components as described in more detail below (for example an inspiratory tube, an expiratory tube, a bubbler)

In some configurations, a respiratory device configured to deliver a respiratory therapy to a patient via a patient interface can comprise a controller; a blower including a motor, wherein a motor speed of the blower can be controlled by the controller; a pressure sensor configured to measure a pressure of gas flow downstream of the blower; wherein the controller can be configured to: compare the pressure against a threshold; reduce a target motor speed of the blower in response to the pressure exceeding the threshold; and control the motor speed to achieve a target flow rate in response to the pressure not exceeding the threshold.

In some configurations, a respiratory device configured to deliver a respiratory therapy to a patient via a patient interface, the device can comprise: a controller; a blower including a motor, wherein a motor speed of the blower is controlled by the controller to a target motor speed; a pressure sensor configured to measure a pressure of gas flow downstream of the blower; wherein the controller is configured to: compare the pressure against a threshold; reduce the target motor speed of the blower in response to the pressure exceeding the threshold; and adjust the target motor speed to achieve a target flow rate in response to the pressure not exceeding the threshold.

In some configurations, a respiratory device configured to deliver a respiratory therapy to a patient via a patient interface, the device can comprise: a controller; a blower, wherein the blower is controlled by the controller; a pressure sensor configured to measure a pressure of gas flow downstream of the blower; wherein the controller is configured to: compare the pressure against a threshold; if the pressure exceeds the pressure threshold, control the blower to reduce the pressure below the threshold; and if the pressure does not exceed the threshold, control the blower to achieve a target flow rate.

In some configurations, the blower comprises a motor.

In some configurations, the blower is controlled by controlling one or more of: motor speed, motor current, and/or motor voltage to a target motor speed, a target motor current, and/or a target motor voltage.

In some configurations, the target motor speed can be reduced at a constant rate. In some configurations, the target motor speed can be reduced at variable rates.

In some configurations, the controller can be configured to continue reducing the target motor speed until the pressure is below the threshold.

In some configurations, the pressure sensor can be an absolute pressure sensor.

In some configurations, pressure can be measured by taking a difference between readings of the pressure sensor and a second pressure sensor, the pressure sensor and the second pressure sensor both being absolute pressure sensors.

In some configurations, the pressure sensor can be a gauge pressure sensor configured to take a difference between an ambient pressure and the pressure downstream of the blower.

In some configurations, the controller can be configured to receive an input of the target flow rate.

In some configurations, the target flow rate can be set by a user.

In some configurations, the device can comprise an oxygen inlet separate from an ambient inlet.

In some configurations, the blower can be configured to mix ambient air from the ambient air inlet and oxygen from the oxygen inlet.

In some configurations, an $FdO_2$ can be in part dependent on the target flow rate.

In some configurations, the controller can be further configured to control the $FdO_2$ by controlling opening of an oxygen inlet valve.

In some configurations, the target flow rate can be constant.

In some configurations, the device can be coupled to a bubbler and the controller can be configured to detect bubbling by monitoring variation in a flow parameter signal.

In some configurations, the flow parameter signal can comprise a flow signal, a pressure signal, or a combination thereof.

In some configurations, the variation can be a variation of a flow parameter signal amplitude from a threshold value.

In some configurations, the variation can be analyzed in a frequency domain.

In some configurations, the controller can be configured to output a warning in response to absence of bubbling for a predetermined period of time.

In some configurations, the controller can be configured to, based on whether bubbling is detected, output warnings of one or more of: a leak, an occlusion, intermittent bubbling, a suggested and/or automatic flow rate change, and/or the flow rate not meeting an inspiratory demand.

In some configurations, the device can further comprise a humidification chamber.

In some configurations, the device can further comprise one or more flow rate sensors.

In some configurations, the device can be a high flow respiratory device.

In some configurations, the system comprises a battery.

In some configurations, the battery is a main source of power for the device.

In some configurations, the battery is an auxiliary source of power for the device.

In some configurations, the device comprises a motor speed limit.

In some configurations, the motor speed limit is based on the or an ambient pressure.

In some configurations, a system can include any configurations of the device as described above. The system can further comprise an inspiratory conduit for providing the gas flow to the patient interface.

In some configurations, the patient interface can form a seal on or around a patient's face.

In some configurations, the patient interface can be configured to connect to an expiratory conduit.

In some configurations, the expiratory conduit can be configured to connect to a bubbler.

In some configurations, the system may not comprise a pressure relief valve between the blower and the patient interface.

In some configurations, a method of providing bubble CPAP via a patient interface coupled to a respiratory device including a flow generator, the flow generator comprising a motor in electrical communication with a controller of the respiratory device, can comprise measuring a pressure of gas flow downstream of the flow generator based on readings from a pressure sensor; comparing the pressure against a threshold; reducing a target motor speed of the flow generator in response to the pressure exceeding the threshold; and controlling a motor speed to achieve a target flow rate in response to the pressure not exceeding the threshold.

In some configurations, a method of providing bubble CPAP via a patient interface coupled to a respiratory device including a flow generator, the flow generator comprising a motor in electrical communication with a controller of the respiratory device, the controller configured to control the motor to a target motor speed, the method can comprise measuring a pressure of gas flow downstream of the flow generator based on readings from a pressure sensor; comparing the pressure against a threshold; reducing the target motor speed of the flow generator in response to the pressure exceeding the threshold; and adjusting the target motor speed to achieve a target flow rate in response to the pressure not exceeding the threshold.

In some configurations, a method of providing bubble CPAP via a patient interface coupled to a respiratory device including a flow generator, the flow generator comprising a blower, optionally the blower comprising a motor, in electrical communication with a controller of the respiratory device, the controller configured to control the motor to a target motor speed, the method can comprise measuring a pressure of gas flow downstream of the flow generator based on readings from a pressure sensor; compare the pressure against a threshold; if the pressure exceeds the pressure threshold, control the blower to reduce the pressure below the threshold; and if the pressure does not exceed the threshold, control the blower to achieve a target flow rate.

In some configurations, the blower is controlled by controlling one or more of: motor speed, motor current, and/or motor voltage to a target motor speed, a target motor current, and/or a target motor voltage.

In some configurations, the target motor speed can be reduced at a constant rate. In some configurations, the target motor speed can be reduced at variable rates.

In some configurations, the method can include continuing reducing the target motor speed until the pressure is below the threshold.

In some configurations, the pressure sensor can be an absolute pressure sensor.

In some configurations, measuring can comprise taking a difference between readings of the pressure sensor and a second pressure sensor, the pressure sensor and the second pressure sensor both being absolute pressure sensors.

In some configurations, the pressure sensor can be a gauge pressure sensor configured to take a difference between an ambient pressure and the pressure downstream of the flow generator.

In some configurations, the target flow rate can be constant.

In some configurations, the method can include receiving an input of the target flow rate.

In some configurations, the target flow rate can be set by a user.

In some configurations, controlling can comprise running a PID controller based on a difference between the target flow rate and a flow rate delivered to a patient measured by one or more flow rate sensors to determine a desired motor speed.

In some configurations, the device can comprise an oxygen inlet separate from an ambient inlet.

In some configurations, the flow generator can be configured to mix ambient air from the ambient air inlet and oxygen from the oxygen inlet.

In some configurations, an $FdO_2$ can be in part dependent on the target flow rate.

In some configurations, the method can further comprise controlling the $FdO_2$ by controlling opening of an oxygen inlet valve.

In some configurations, the method can further comprise detecting bubbling in a bubbler coupled to the respiratory device by monitoring variation in a flow parameter signal.

In some configurations, the flow parameter signal can comprise a flow signal, a pressure signal, or a combination thereof.

In some configurations, the variation can be a variation of a flow parameter signal amplitude from a threshold value.

In some configurations, the variation can be analyzed in a frequency domain.

In some configurations, the method can further comprise outputting a warning in response to absence of bubbling for a predetermined period of time.

In some configurations, the method can further comprise, based on whether bubbling is detected, outputting warnings of one or more of: a leak, an occlusion, intermittent bubbling, a suggested and/or automatic flow rate change, and/or the flow rate not meeting an inspiratory demand.

In some configurations, the device can further comprise a humidification chamber.

In some configurations, the device comprises a battery.

In some configurations, the battery is a main source of power for the device.

In some configurations, the battery is an auxiliary source of power for the device.

In some configurations, the device comprises a motor speed limit.

In some configurations, the motor speed limit is based on the or an ambient pressure.

In some configurations, the device can be comprised in a respiratory system including the patient interface, the system not comprising a pressure relief valve between the flow generator and the patient interface.

In some configurations, the respiratory device can be coupled to an inspiratory conduit for providing a flow of gas to the patient interface.

In some configurations, the patient interface can form a seal on or around a patient's face.

In some configurations, the patient interface can be configured to connect to an expiratory conduit.

In some configurations, the expiratory conduit can be configured to connect to a bubbler.

In some configurations, a respiratory system configured to deliver bubble CPAP therapy to a patient via a patient interface can comprise a respiratory device comprising: a controller, a blower including a motor, wherein a motor speed of the blower can be controlled by the controller, the blower configured to generate a flow of gas to the patient at a target flow rate, and a housing enclosing the controller and the blower; an inspiratory conduit for providing the gas flow to the patient interface; and an expiratory conduit having a proximal end and a distal end, the proximal end being coupled to the patient interface and the distal end submerged to a predetermined depth of a column of water.

In some configurations, the system can further a pressure sensor configured to measure a pressure of the flow of gas downstream of the blower, wherein the controller can be configured to: compare the pressure against a threshold; reduce a target motor speed of the blower in response to the pressure exceeding the threshold; and control the motor speed to achieve the target flow rate in response to the pressure not exceeding the threshold.

In some configurations, a respiratory system configured to deliver bubble CPAP therapy to a patient via a patient interface can comprise a respiratory device comprising: a controller, a blower including a motor, wherein a motor speed of the blower can be controlled by the controller to a target motor speed, the blower configured to generate a flow of gas to the patient at a target flow rate, and a housing enclosing the controller and the blower; an inspiratory conduit for providing the gas flow to the patient interface; and an expiratory conduit having a proximal end and a distal end, the proximal end being coupled to the patient interface and the distal end submerged to a predetermined depth of a column of water.

The blower comprises an inlet for drawing in ambient air and driving ambient air to the patient via a patient conduit (i.e. an inspiratory conduit) by the blower. The controller controls the blower to a target motor speed or a target flow or both. The controller preferably provides control signals to control i.e. vary the current or voltage or power provided to the motor of the blower in order achieve the target motor speed or target flow rate. The respiratory system may also optionally include a supplementary gases inlet to receive supplementary gases e.g. oxygen. The blower is configured to receive ambient gases and supplementary gases and mix these together.

In some configurations, the system can further a pressure sensor configured to measure a pressure of the flow of gas downstream of the blower, wherein the controller can be configured to: compare the pressure against a threshold; reduce a target motor speed of the blower in response to the pressure exceeding the threshold; and adjust the target motor speed to achieve the target flow rate in response to the pressure not exceeding the threshold.

In some configurations, the system can further a pressure sensor configured to measure a pressure of the flow of gas downstream of the blower, wherein the controller can be configured to: compare the pressure against a threshold; if the pressure exceeds the pressure threshold, control the blower to reduce the pressure below the threshold; and if the pressure does not exceed the threshold, control the blower to achieve a target flow rate.

In some configurations, the blower is controlled by controlling one or more of: motor speed, motor current, and/or motor voltage to a target motor speed, a target motor current, and/or a target motor voltage.

In some configurations, the target motor speed can be reduced at a constant rate. In some configurations, the target motor speed can be reduced at variable rates.

In some configurations, the controller can be configured to continue reducing the target motor speed until the pressure is below the threshold.

In some configurations, the pressure sensor can be an absolute pressure sensor.

In some configurations, pressure can be measured by taking a difference between readings of the pressure sensor and a second pressure sensor, the pressure sensor and the second pressure sensor both being absolute pressure sensors.

In some configurations, the pressure sensor can be a gauge pressure sensor configured to take a difference between an ambient pressure and the pressure downstream of the blower.

In some configurations, the target flow rate can be constant.

In some configurations, the controller can be configured to receive an input of the target flow rate.

In some configurations, the target flow rate can be set by a user.

In some configurations, the device can comprise an oxygen inlet separate from an ambient inlet.

In some configurations, the blower can be configured to mix ambient air from the ambient air inlet and oxygen from the oxygen inlet.

In some configurations, an $FdO_2$ can be in part dependent on the target flow rate.

In some configurations, the controller can be further configured to control the $FdO_2$ by controlling opening of an oxygen inlet valve.

In some configurations, the system can comprise a bubbler, the column of water contained in the bubbler.

In some configurations, the controller can be configured to detect bubbling by monitoring variation in a flow parameter signal.

In some configurations, the flow parameter signal can comprise a flow signal, a pressure signal, or a combination thereof.

In some configurations, the variation can be a variation of a flow parameter signal amplitude from a threshold value.

In some configurations, the variation can be analyzed in a frequency domain.

In some configurations, the controller can be configured to output a warning in response to absence of bubbling for a predetermined period of time.

In some configurations, the controller can be configured to, based on whether bubbling is detected, output warnings of one or more of: a leak, an occlusion, intermittent bubbling, a suggested and/or automatic flow rate change, and/or the flow rate not meeting an inspiratory demand.

In some configurations, the patient interface can form a seal on or around a patient's face.

In some configurations, the device can further comprise a humidification chamber.

In some configurations, the device can further comprise one or more flow rate sensors.

In some configurations, the system may not comprise a pressure relief valve between the blower and the patient interface.

In some configurations, the device can be a high flow respiratory device.

In some configurations, the device comprises a battery.

In some configurations, the battery is a main source of power for the device.

In some configurations, the battery is an auxiliary source of power for the device.

In some configurations, the device comprises a motor speed limit.

In some configurations, the motor speed limit is based on the or an ambient pressure.

In some configurations a respiratory system configured to deliver high flow therapy or Bubble CPAP therapy, wherein the respiratory system comprises: a respiratory device that comprises a flow generator, a humidifier in fluid communication with the flow generator, a controller in electronic control with the flow generator, an inspiratory conduit in fluid communication with the humidifier, the respiratory device changeable between a high flow therapy mode and a Bubble CPAP therapy mode, wherein in the high flow therapy mode the respiratory device is configured to provide high flow therapy and in the Bubble CPAP therapy mode the respiratory device is configured to provide bubble CPAP therapy.

In some configurations, the high flow therapy is nasal high flow therapy.

In some configurations, the respiratory device comprises a housing, the flow generator and humidifier integrated into the housing. The controller is also positioned within the housing. The humidifier may comprise a heater plate and a humidification chamber. The heater plate being positioned within the housing. The housing defining a chamber bay and the heater plate located in the chamber bay. The humidification chamber being removably positioned on the heater plate. The housing comprises a gases outlet, and the inspiratory conduit connectable to the outlet.

In the high flow therapy mode the system comprises an unsealed patient interface coupled to the inspiratory conduit.

In the high flow therapy mode the system comprises an unsealed patient interface coupled to the inspiratory conduit.

In some configurations, the unsealed patient interface may be a nasal cannula.

In some configurations, in use, the nasal cannula is positioned on the user's face to provide gases to the nares of the user.

In the Bubble CPAP therapy mode the system comprises a sealed patient interface coupled to the inspiratory conduit, an expiratory conduit coupled to the sealed patient interface, and wherein the expiratory conduit is coupled to a pressure regulator to regulate pressure within the patient interface and/or the patient's airways.

In some configurations, pressure regulator comprises a chamber with a column of water and the expiratory conduit being submerged into the column of water. The pressure provided to the user being defined or being set by the depth the submersion of the expiratory conduit within the column of water.

In some configurations, the inspiratory conduit is common between the high flow therapy mode and the bubble CPAP therapy mode.

In some configurations, the controller comprises a high flow therapy control program associated with the high flow therapy mode.

In some configurations, the controller comprises a bubble CPAP therapy control program associated with the bubble CPAP therapy mode.

In some configurations, the controller is configured to select and apply a program that corresponds to the selected mode of operation.

In some configurations, each program defines operating parameters.

In some configurations, operating parameters may comprise one or more motor speed or pressure limits (for example a pressure cap).

In some configurations, operating parameters may comprise one or more alarm conditions.

In some configurations, one or more alarm conditions may comprise a lack of bubbling in the bubble CPAP therapy mode.

In some configurations, operating parameters may define a humidity level.

In some configurations, operating parameters may one or more temperature or dew point set points to control the humidifier.

In some configurations, the humidity level provided during the high flow mode may be greater than the humidity level provided during bubble CPAP therapy mode.

In some configurations, the operating parameters may also define a flow limit in each mode.

In some configurations, the controller is configured to detect bubbling of the bubbler, and wherein if bubbling is detected the controller selects the bubble CPAP therapy mode.

In some configurations, the controller may automatically switch mode if a bubbler is detected by bubbling.

In some configurations, a user can select the high flow therapy mode, or the bubble CPAP therapy mode (optionally via a user interface).

In some configurations, the controller is configured to detect bubbling by monitoring variation in a flow parameter signal.

In some configurations, the flow parameter signal comprises a flow signal, a pressure signal, or a combination thereof.

In some configurations, the variation is a variation of a flow parameter signal amplitude from a threshold value.

In some configurations, the variation is analyzed in a frequency domain.

In some configurations the same inspiratory conduit may be used for bubble CPAP mode and for high flow mode. The same inspiratory conduit being useable for both modes reduces the number of components that are required to be interchanged when changing mode. Further this common inspiratory conduit allows the same respiratory device comprising a blower and humidifier integrated into a housing to be used for both bubble CPAP mode and high flow mode. Further the integrated humidifier and blower in a common housing makes it simple to transition between bubble CPAP and high flow modes since a single device can be used, rather than unique set ups of several components as required in prior art systems. The present system provides a single respiratory device that can be used to deliver both bubble CPAP therapy and high flow therapy, while only the interface requiring changes. There is no changes in components on the gases supply side i.e. no changes in the gases supply components since a common respiratory device can be used to deliver humidified gases.

In some configurations, a high flow therapy mode kit for use with a respiratory device comprises one or more of: a non-sealing patient interface, an inspiratory conduit.

In some configurations, the high flow therapy mode kit is used in the high flow therapy mode (as described elsewhere in the specification).

In some configurations, a bubble CPAP therapy mode kit for use with a respiratory device comprises one or more of: a sealing patient interface, an inspiratory conduit, a expiratory conduit, and/or a bubbler.

In some configurations, the bubble CPAP therapy mode kit is used in the bubble CPAP therapy mode (as described elsewhere in the specification).

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

DETAILED DESCRIPTION

Although certain examples are described below, those of skill in the art will appreciate that the disclosure extends beyond the specifically disclosed examples and/or uses and obvious modifications and equivalents thereof. Thus, it is intended that the scope of the disclosure herein disclosed should not be limited by any particular examples described below.

Bubble CPAP therapy can produce variations or oscillations in the pressure of gases supplied to a patient connected to a positive pressure ventilation device. By submerging one end of the expiratory conduit into a water column, the resulting bubbles generate a variation or ripple in the pressure of gases delivered to the patient. The bubble CPAP system also provides a method of varying a mean pressure of gases supplied to the patient by variation of the level to which the end of the expiratory conduit is submerged within the water column. The level of submergence of the end of the expiratory conduit can be kept constant in order to maintain the mean pressure of gases supplied to the patient.

Figure 1:
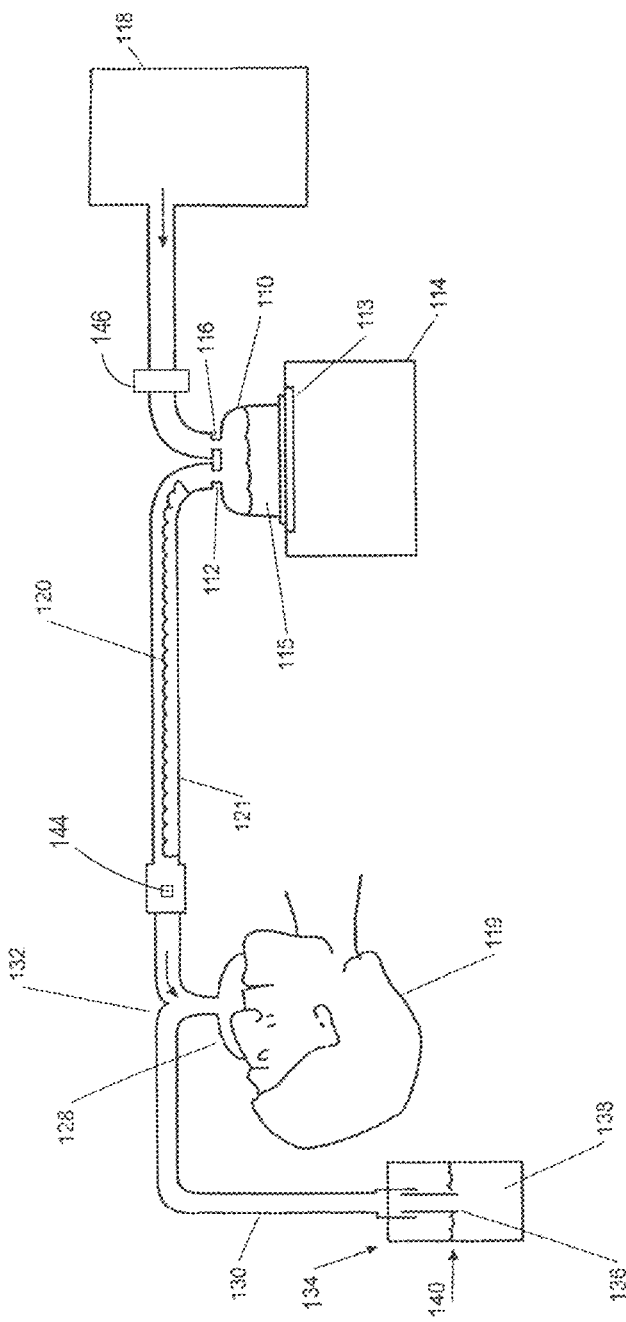
FIG. 1 illustrates schematically a conventional setup of using a respiratory apparatus to provide bubble CPAP.

As shown in FIG. 1, a conventional respiratory system for providing bubble CPAP therapy can provide to a patient 119 humidified and pressurized gas through a patient interface, such as a mask 128 in FIG. 1 connected to an inspiratory conduit 121. The inspiratory conduit 121 is connected to the outlet 112 of a humidification chamber 110, which contains a volume of water 115. As the volume of water 115 within the humidification chamber 110 is heated by a heater plate 113 in the device housing 114, water vapor begins to fill the volume of the chamber 110 above the water's surface. The water vapor can heat and humidify a flow of gas (for example, air) provided from a wall source 118 (see FIG. 1) into the chamber 110 through an inlet 116 of the chamber 110. The heated and humidified gas is passed out of an outlet 112 of the humidification chamber 110 into the inspiratory conduit 121. The inspiratory conduit 121 may contain a heater, such as heater wires 120 in FIG. 1, which heat the walls of the conduit to promote a substantially constant humidity profile along the inspiratory conduit 121 and therefore reduce condensation of the humidified gas within the inspiratory conduit 121. The device can supply power to heat the inspiratory conduit 121 and the heater plate 113, such as through input from one or more sensors in the system, as will be described in further detail below.

The humidified gas can pass through the inspiratory conduit 121 to a patient interface, such as the mask 128, attached and/or sealed around the patient's 119 mouth, nose, and/or nares. The inspiratory conduit 121 provides the patient 119 with a flow of gas that may by ambient air, oxygen, a mixture of the two, or a mixture of ambient air and other auxiliary gas(es). The gas may include medicaments, which may be added through nebulization. The flow of gas through the inspiratory conduit 121 can be delivered at a substantially constant flow rate in a bubble CPAP. As shown in FIG. 1, a setup has a flow of gas supplied by the wall source 118. The wall source 118 can deliver the gas at the target flow rate so as to maintain the flow rate of gas delivered to the patient.

As shown in FIG. 1, excess gas can flow through the expiratory conduit 130 to a pressure regulator 134, which is a bubbler in the illustrated example. In a bubble CPAP system, the expiratory conduit 130 can terminate in an open terminal end 136. This terminal end 136 can be submerged in a volume of water 138 inside the bubbler 134.

The bubbler can regulate pressure by the terminal end 136 of the expiratory conduit 130 submerged at a desired depth under the water level 140 within the volume of water 138. The terminal end 136 can also optionally be located on a short conduit that can be integrated into the end of the expiratory conduit 130. The bubbler can act as a pressure regulator by venting out gas whenever the pressure exceeds the desired level so as to maintain the average or mean pressure at the target level. The bubble CPAP system can also include a pressure relief valve 146 for venting excess gas when the pressure exceeds the desired level. The bubbler can also provide oscillations in the pressure, which may have clinical benefits. Bubble CPAP therapy may lower the incidence of acute lung injury and bronchopulmonary dysplasia, compared with intubation and/or mechanical ventilation.

Overview of Example Flow Therapy Apparatus

Figure 2:
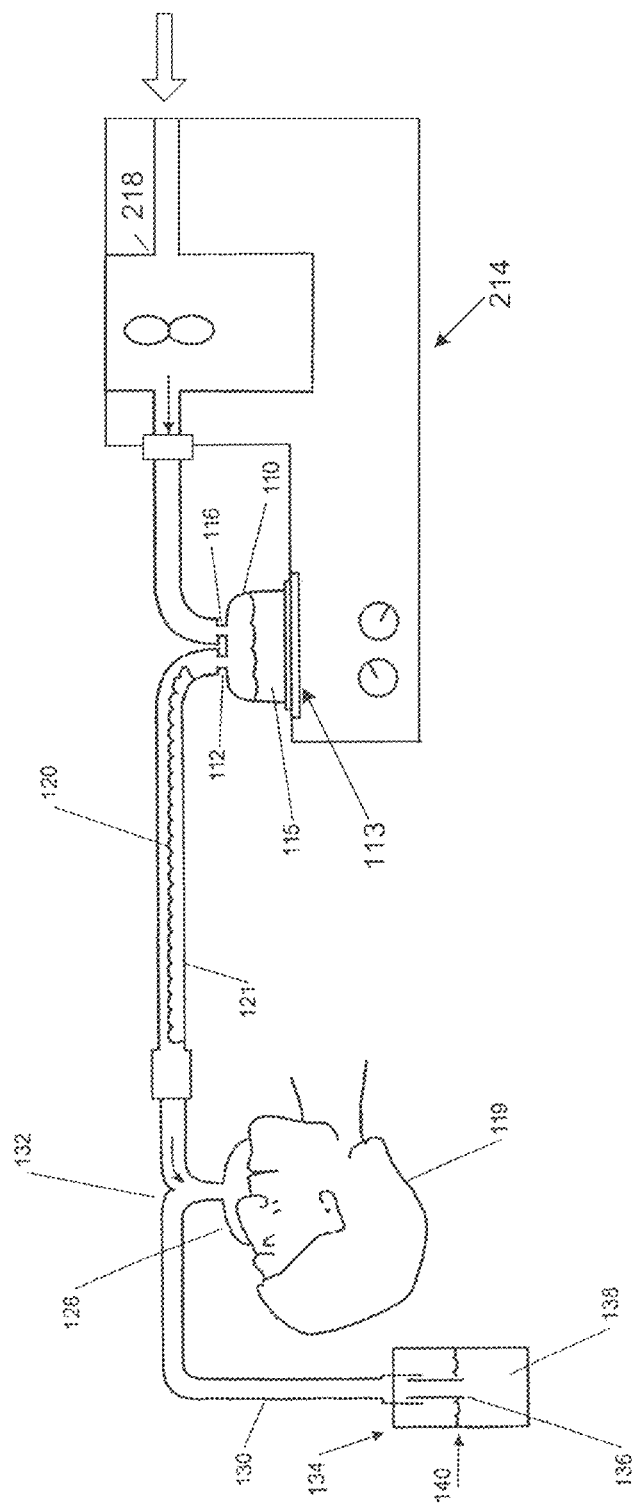
FIG. 2 illustrates schematically a respiratory apparatus with a flow generator to provide bubble CPAP.

FIG. 2 illustrates an example respiratory apparatus with a flow generator 218 (also referred to as a blower but can include other types of flow generator disclosed herein) configured to provide bubble CPAP. Using a flow generator to generate the flow of gas can allow the respiratory apparatus to be used without a wall source to provide bubble CPAP, such as in circumstances where a wall source is not available. Further, using a flow generator e.g. a blower in a respiratory apparatus allows the respiratory apparatus to draw in ambient air and provide ambient air as a flow of gases for bubble CPAP. This allows the respiratory apparatus to be simpler and cheaper to use as there is no requirement for a gas store or a gas source e.g. a wall source. Further the respiratory apparatus with a flow generator e.g. a blower is advantageous because there is no risk of running out of gases, since ambient air is provided to the patient. This ensures there is no disruption in therapy due to a gas source being empty, since ambient air is abundant. By integrating the humidifier, and optionally a supplementary gases blender (for example, by integrating an oxygen inlet port 358' shown in FIG. 3C), into the flow generator, fewer separate components are needed in the system, which simplifies its setup. Further the system occupies less space because there are less separate components connected by tubes. The described respiratory apparatus with an integrated humidifier and optionally an integrated supplementary gas blender can occupy less space and reduces additional interconnecting tubes. Additionally, the flow generator, integrated humidifier, and supplementary gases blender can be controlled by a single controller, which allows for additional monitoring and control of various flow parameters, as will be described further. Additionally, the respiratory apparatus including a flow generator may be able to provide other forms of therapy, such as a nasal high flow therapy, thereby making for an easier transition between different types of respiratory support as the patient's condition changes, and may also reduce the number of consumable components required, for example a common heated breathing tube may be used across multiple therapies, requiring only the patient interface to be changed.

The respiratory system in FIG. 2 can differ from the conventional bubble CPAP setup in FIG. 1 at least by having the flow of gas provided by the blower 218 integrated within the device housing 214. The system in FIG. 2 can also optionally include a supplementary gas source (such as an oxygen tank, an oxygen blender coupled to a flowmeter, and the like) for controlling oxygen concentration in the flow of gas delivered to the patient 119. The supplemental gas source can be connected to the device housing 214 and/or to the blower 218 (for example at a supplementary gas inlet). The supplementary gas source can also be configured to provide other types of auxiliary gas, such as nitrogen. The supplementary gas source may be connected to an internal blender that blend ambient air and the supplementary gases to provide a gases flow to a patient. The concentration of the supplementary gases introduced into, or present in, the gases stream can be controlled. The system can include a temperature sensor, such as the temperature sensor 144 of FIG. 1, in the inspiratory conduit 121. The temperature sensor 144 can be coupled to and in electrical communication with a controller located in the device housing 214.

In some embodiments the blower is configured to receive the ambient gases and supplementary gases and mix these together.

The respiratory system in FIG. 2 can include a high flow system. A schematic representation of a high flow system 10 is provided in FIG. 3A. The respiratory system 10 can include a main device housing 100. The main device housing 100 can contain a flow generator 11 that can be in the form of a motor/impeller arrangement (such as a blower), an optional humidifier or humidification chamber 12, a controller 13, and a user interface 14. The user interface 14 can include a display and input device(s) such as button(s), a touch screen, a combination of a touch screen and button(s), or the like. The controller 13 can include one or more hardware and/or software processors and can be configured or programmed to control the components of the apparatus, including but not limited to operating the flow generator 11 to create a flow of gas for delivery to a patient, operating the humidifier 12 (if present) to humidify and/or heat the gas flow, receiving user input from the user interface 14 for reconfiguration and/or user-defined operation of the respiratory system 10, and outputting information (for example on the display) to the user. The user can be a patient, healthcare professional, or others.

Figure 3A:
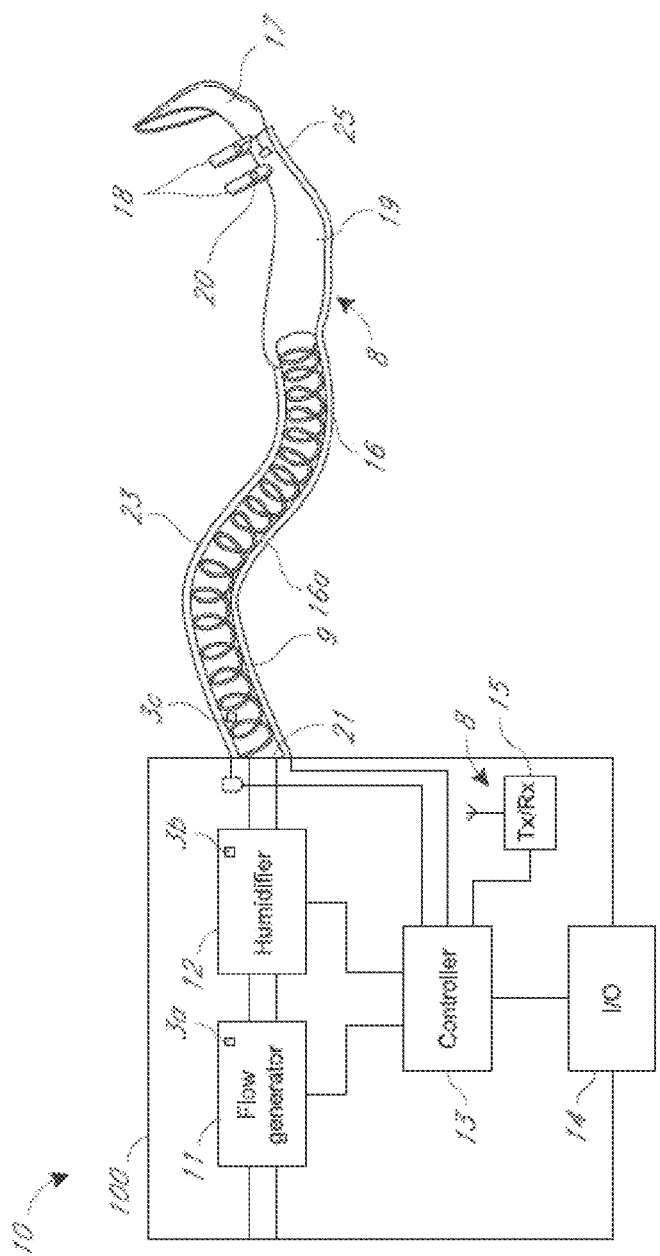
FIG. 3A illustrates schematically a high flow respiratory system configured to provide a respiratory therapy to a patient.

With continued reference to FIG. 3A, a patient breathing conduit 16 can be coupled to a gases flow outlet 21 in the main device housing 100 of the respiratory system 10, and be coupled to a patient interface 17. The patient interface can be a non-sealing interface like a nasal cannula with a manifold 19 and nasal prongs 18 for providing a high flow therapy. The nasal cannula does not completely seal the nostrils of the user such that exhaled gases leak out from around the nasal prongs when the user exhales. The patient breathing conduit 16 can also be coupled to a sealing interface like a face mask, an oro-nasal mask, a nasal mask, a nasal pillow mask, or a nasal cannula for providing bubble CPAP. The patient interface can also optionally include an endotracheal tube, a tracheostomy interface, or others.

The flow of gas can be generated by the flow generator 11, and may be humidified, before being delivered to the patient via the patient conduit 16 through the patient interface 17. The controller 13 can control the flow generator 11 to generate a gas flow of a desired flow rate, and/or one or more valves to control mixing of air and oxygen or other breathable gas. The controller 13 can control a heating element in the humidification chamber 12, if present, to heat the gases to a desired temperature that achieves a desired level of temperature and/or humidity for delivery to the patient. The patient conduit 16 can have a heating element 16a, such as a heater wire, to heat gases flow passing through to the patient. The heating element 16a can also be under the control of the controller 13. The heating element 16a heats gases to reduce and/or prevent condensation within the patient conduit 16.

The system 10 can use ultrasonic transducer(s), flow sensor(s) such as a thermistor flow sensor, pressure sensor(s), temperature sensor(s), humidity sensor(s), or other sensors, in communication with the controller 13, to monitor characteristics of the gas flow and/or operate the system 10 in a manner that provides suitable therapy. The gas flow characteristics can include gases concentration, flow rate, pressure, temperature, humidity, or others. The sensors 3a, 3b, 3c, 20, 25, such as pressure, temperature, humidity, and/or flow sensors, can be placed in various locations in the main device housing 100, the patient conduit 16, and/or the patient interface 17. The controller 13 can receive output from the sensors to assist it in operating the respiratory system 10 in a manner that provides suitable therapy, such as to determine a suitable target temperature, flow rate, and/or pressure of the gases flow. Providing suitable therapy can include meeting a patient's inspiratory demand. The suitable therapy flow rates, such as a high flow therapy flow rate, and/or a flow rate meeting or exceeding the patient's inspiratory demand, are explained below.

The system 10 can include a wireless data transmitter and/or receiver, or a transceiver 15 to enable the controller 13 to receive data signals 8 in a wireless manner from the operation sensors and/or to control the various components of the system 10. Additionally, or alternatively, the data transmitter and/or receiver 15 can deliver data to a remote server or enable remote control of the system 10. In one example the remote server can record patient usage data e.g. usage of the bubble CPAP system or usage of the high flow system. Usage can be usage time and/or also include flow rate and humidity level (e.g. dew point). The system 10 can also include a wired connection, for example, using cables or wires, to enable the controller 13 to receive data signals 8 from the operation sensors and/or to control the various components of the system 10.

The system 10 can be powered from mains voltage.

In some embodiments, the system can include an auxiliary power source (for example a battery).

In some embodiments, the system can include a battery. The battery may provide the main source of power for the system, or may serve as an auxiliary source of power when the main source of power is unavailable. This is advantageous because therapy can be continued to be delivered i.e. gases can be continue to be delivered to a patient even if there is a shortage or outage in mains power. This is advantageous because therapy can be maintained for a period of time for neonatal or infants thereby reducing the chances or physiological deterioration or harm occurring to these patient's due to loss of therapy.

The battery can increase portability of the system to allow for the system to be used in situations where a mains voltage power source is unavailable.

High flow therapy as discussed herein is intended to be given its typical ordinary meaning as understood by a person of skill in the art which generally refers to a respiratory assistance system delivering a targeted flow of humidified respiratory gases via an intentionally unsealed patient interface with flow rates generally intended to meet or exceed inspiratory flow of a patient. Typical patient interfaces include, but are not limited to, a nasal or tracheal patient interface. Typical flow rates for adults often range from, but are not limited to, about fifteen liters per minute to about sixty liters per minute or greater. Typical flow rates for pediatric patients (such as neonates, infants and children) often range from, but are not limited to, about one liter per minute per kilogram of patient weight to about three liters per minute per kilogram of patient weight or greater. High flow therapy can also optionally include gas mixture compositions including supplemental oxygen and/or administration of therapeutic medicaments. High flow therapy is often referred to as nasal high flow (NHF), humidified high flow nasal cannula (HHFNC), high flow nasal oxygen (HFNO), high flow therapy (HFT), or tracheal high flow (THF), among other common names.

As used herein, "high flow" therapy may also refer to administration of gas to the airways of a patient at a relatively high flow rate that optionally meets or exceeds the peak inspiratory demand of the patient. Some example flow rates used to achieve "high flow" may be any of the flow rates listed below. For example, in some configurations, for an adult patient 'high flow therapy' may refer to the delivery of gas(es) to a patient at a flow rate of greater than or equal to about 10 litres per minute (10 LPM), such as between about 10 LPM and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. In some configurations, for a neonatal, infant, or child patient 'high flow therapy' may refer to the delivery of gas(es) to a patient at a flow rate of greater than 1 LPM, such as between about 1 LPM and about 25 LPM, or between about 2 LPM and about 25 LPM, or between about 2 LPM and about 5 LPM, or between about 5 LPM and about 25 LPM, or between about 5 LPM and about 10 LPM, or between about 10 LPM and about 25 LPM, or between about 10 LPM and about 20 LPM, or between about 10 LPM and 15 LPM, or between about 20 LPM and 25 LPM. A high flow therapy apparatus with an adult patient, a neonatal, infant, or child patient, may deliver gas(es) to the patient at a flow rate of between about 1 LPM and about 100 LPM, or at a flow rate in any of the sub-ranges outlined above.

Figure 3B:
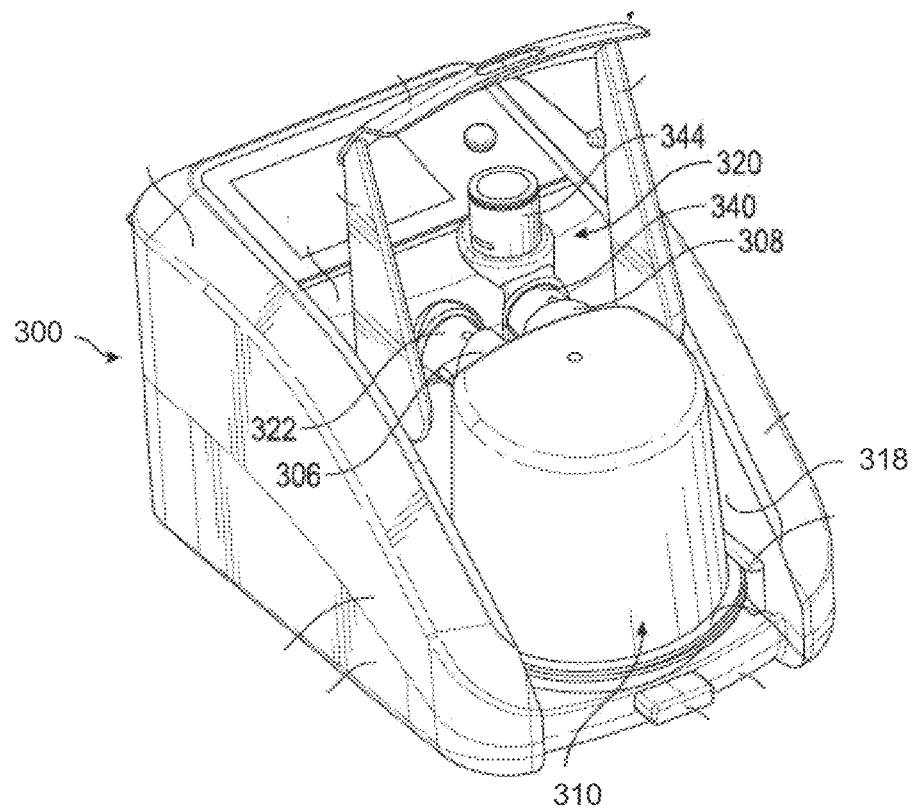
FIG. 3B is a front perspective view of an example high flow respiratory apparatus with a humidification chamber in position.
Figure 3C:
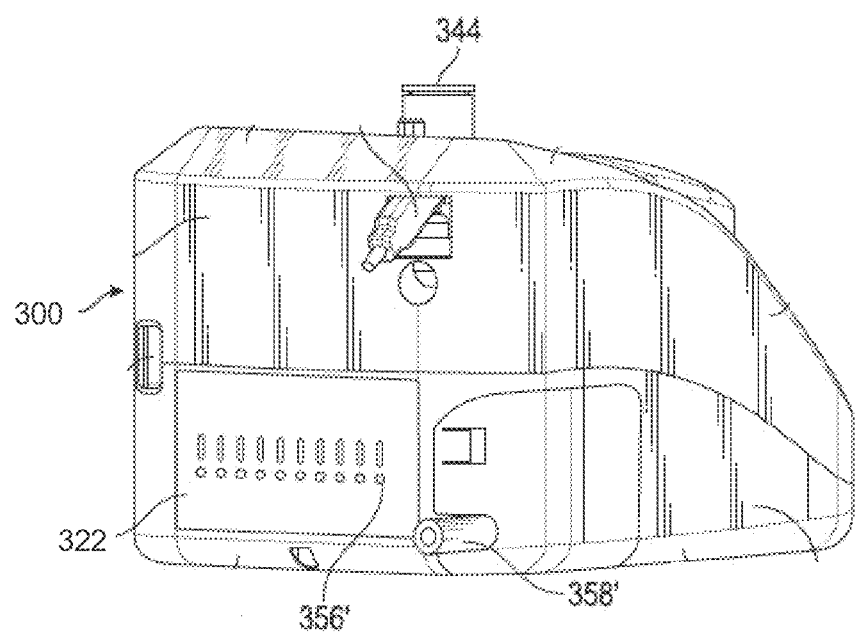
FIG. 3C is a back perspective view of the respiratory apparatus of FIG. 3B.

FIGS. 3B and 3C show an example respiratory device of the respiratory system 10. The device can include a housing 300, which encloses a flow generator. The flow generator may include a motor and/or sensor module. The motor and/or sensor module may be non-removable from the main housing 300. The motor and/or sensor module can also optionally be removable from the main housing 300. The housing 300 can include a humidifier or humidification chamber bay 318 for receipt of a removable humidification chamber 310. The removable humidification chamber 310 contains a suitable liquid such as water for heating and humidifying gases delivered to a patient. The humidification chamber 310 can be fluidly coupled to the device housing 300 in a linear slide-on motion into the chamber bay 318. A gas outlet port 322 can establish a fluid communication between the motor and/or sensor module and an inlet 306 of the chamber 310.

Heated and humidified gas can exit an outlet 308 of the chamber 310 into a humidified gas return 340, which can include a removable L-shaped elbow. The removable elbow can further include a patient outlet port 344 for coupling to the inspiratory conduit, such as the inspiratory conduit 16 of FIG. 3A to deliver gases to the patient interface 17. The gas outlet port 322, humidified gas return 340, and patient outlet port 344 each can have seals such as O-ring seals or T-seals to provide a sealed gases passageway between the device housing 300, the humidification chamber 310, and the inspiratory conduit. A floor portion of the humidification chamber bay 318 in the housing 300 can include a heater arrangement such as a heater plate or other suitable heating element(s) for heating the water in the humidification chamber 310 for use during a humidification process. The elbow may comprise one or more integrated sensors. For example the elbow may comprise a pair of embedded temperature sensors.

As shown in FIG. 3C, the device can include an arrangement to enable the flow generator to deliver air, oxygen (or alternative auxiliary gas), or a suitable mixture thereof to the humidification chamber 310 and thereby to the patient. This arrangement can include an air inlet 356' in a rear wall 322 of the housing 300. The device can include a separate oxygen inlet port 358'. In the illustrated configuration, the oxygen inlet port 358' can be positioned adjacent one side of the housing 300 at a rear end thereof. The oxygen port 358' can be connected to an oxygen source such as a tank, or an oxygen blender. The oxygen inlet port 358' can be in fluid communication with a valve. The valve can suitably be a solenoid valve that enables the control of the amount of oxygen that is added to the gas flow that is delivered to the humidification chamber 310.

The housing 300 can include suitable electronics boards, such as sensing circuit boards. The electronics boards can contain, or can be in electrical communication with, suitable electrical or electronics components, such as but not limited to microprocessors, capacitors, resistors, diodes, operational amplifiers, comparators, and switches. One or more sensors can be used with the electronic boards. Components of the electronics boards (such as but not limited to one or more microprocessors) can act as the controller 13 of the apparatus. One or both of the electronics boards can be in electrical communication with the electrical components of the system 10, including but not limited to the display unit and user interface 14, motor, valve, and the heater plate to operate the motor to provide the desired flow rate of gases, humidify and heat the gases flow to an appropriate level, and supply appropriate quantities of oxygen (or quantities of an alternative auxiliary gas) to the gases flow.

As mentioned above, operation sensors, such as flow, temperature, humidity, and/or pressure sensors can be placed in various locations in the respiratory device, the patient conduit 16, and/or cannula 17. The electronics boards can be in electrical communication with those sensors. Output from the sensors can be received by the controller 13, to assist the controller 13 to operate the respiratory system 10 in a manner that provides optimal therapy, including meeting inspiratory demand. One or more sensors (for example, Hall-effect sensors) may be used to measure a motor speed of the motor of the flow generator. The motor may include a brushless DC motor, from which motor speed can be measured without the use of separate sensors. For example, during operation of a brushless DC motor, back-EMF can be measured from the non-energized windings of the motor, from which a motor position can be determined, which can in turn be used to calculate a motor speed. In addition, a motor driver may be used to measure motor current, which can be used with the measured motor speed to calculate a motor torque. The motor may also include a low inertia motor.

Room air can enter the flow generator through the inlet port, such as the air inlet port 356' in FIG. 3C. The flow generator can operate at a motor speed of greater than 1,000 RPM and less than 30,000 RPM, greater than 2,000 RPM and less than 21,000 RPM, greater than 4,000 RPM and less than 15000 RPM, or between any of the foregoing values. Operation of the flow generator can mix the gases entering the flow generator, such as the motor and/or sensor chamber through the inlet port. Using the flow generator as the mixer can reduce the pressure drop that would otherwise occur in a system with a separate mixer, such as a static mixer comprising baffles, because mixing requires energy.

Figure 4:
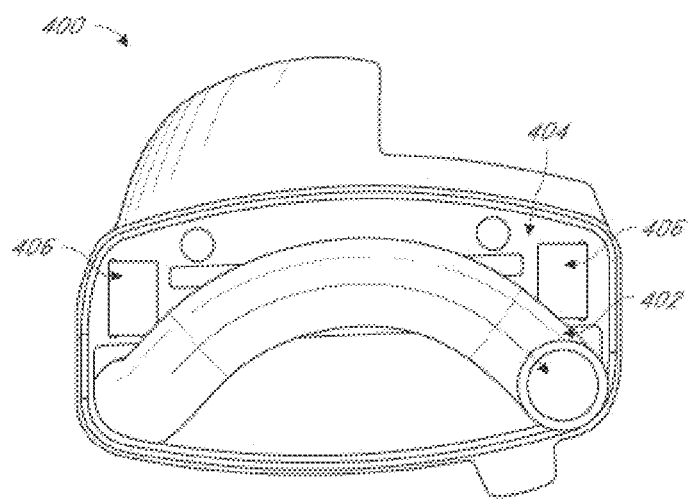
FIG. 4 illustrates an example sensing chamber of the respiratory apparatus of FIG. 3B.

As shown in FIG. 4, the mixed air can exit the flow generator and enter a flow path 402 in a sensor chamber 400, which can be located in the motor and/or sensor module. A sensing circuit board 404 with sensors, such as ultrasonic sensors 406 and/or heated thermistor flow sensors, can be positioned in the sensor chamber 400 such that the sensing circuit board is at least partially immersed in the gas flow. At least some of the sensors on the sensing circuit board can be positioned within the gas flow to measure gas properties within the flow. After passing through the flow path 402 in the sensor chamber 400, the gas can exit to the humidification chamber 310.

Positioning sensors downstream of the flow generator can increase accuracy of measurements, such as the measurement of gases fraction concentration, including oxygen concentration, over systems that position the sensors upstream of the flow generator and/or the mixer. Such a positioning can give a repeatable flow profile. Further, positioning the sensors downstream of the combined flow generator and mixer avoids the effect of the pressure drop that would otherwise occur when sensing occurs prior to the flow generator and a separate mixer. Also, immersing at least part of the sensing circuit board and sensors in the flow path can increase the accuracy of measurements because the sensors being immersed in the flow are more likely to be subject to the same conditions, such as temperature and pressure, as the gas flow and therefore provide a better representation of the gas flow characteristics.

As shown in FIG. 4, the flow path 402 can have a curved shape. The flow path 402 can be configured to have a curved shape with no sharp turns. The flow path 402 can have curved ends with a straighter section between the curved ends. A curved flow path shape can reduce pressure drop in a gas flow without reducing the sensitivity of flow measurements by partially coinciding a measuring region with the flow path to form a measurement portion of the flow path.

The sensing circuit board 404 can include sensors such as acoustic transmitters and/or receivers, humidity sensor, temperature sensor, thermistor, and the like. A gas flow rate may be measured using at least two different types of sensors. The first type of sensor can include a thermistor, which can determine a flow rate by monitoring heat transfer between the gases flow and the thermistor. The thermistor flow sensor can run the thermistor at a constant target temperature within the flow when the gas flows around and past the thermistor. The sensor can measure an amount of power required to maintain the thermistor at the target temperature. The target temperature can be configured to be higher than a temperature of the gas flow, such that more power is required to maintain the thermistor at the target temperature at a higher flow rate.

The thermistor flow rate sensor can also maintain a plurality of (for example, two, three, or more) constant temperatures on a thermistor to avoid the difference between the target temperature and the gas flow temperature from being too small or too large. The plurality of different target temperatures can allow the thermistor flow rate sensor to be accurate across a large temperature range of the gas. For example, the thermistor circuit can be configured to be able to switch between two different target temperatures, such that the temperature of the gas flow can always fall within a certain range relative to one of the two target temperatures (for example, not too close and not too far). The thermistor circuit can be configured to operate at a first target temperature of about 50° C. to about 70° C., or about 66° C. The first target temperature can be associated with a desirable flow temperature range of between about 0° C. to about 60° C., or about 0° C. and about 40° C. The thermistor circuit can be configured to operate at a second target temperature of about 90° C. to about 110° C., or about 100° C. The second target temperature can be associated with a desirable flow temperature range of between about 20° C. to about 100° C., or about 30° C. and about 70° C.

The controller can be configured to adjust the thermistor circuit to change between at least the first and second target temperature modes by connecting or bypassing a resistor within the thermistor circuit. The thermistor circuit can be arranged as a Wheatstone bridge configuration comprising a first voltage divider arm and a second voltage divider arm. The thermistor can be located on one of the voltage divider arms. More details of a thermistor flow rate sensor are described in International Patent No. WO2018052320A2, the entirety of which is incorporated by reference herein.

The second type of sensor can include an acoustic (such as ultrasonic) sensor assembly. Acoustic sensors including acoustic transmitters and/or receivers can be used to measure a time of flight of acoustic signals to determine gas velocity and/or composition, which can be used in flow therapy apparatuses. In one ultrasonic sensing (including ultrasonic transmitters and/or receivers) topology, a driver causes a first sensor, such as an ultrasonic transducer, to produce an ultrasonic pulse in a first direction. A second sensor, such as a second ultrasonic transducer, receives this pulse and provides a measurement of the time of flight of the pulse between the first and second ultrasonic transducers. Using this time of flight measurement, the speed of sound of the gas flow between the ultrasonic transducers can be calculated by a processor or controller of the respiratory apparatus. The second sensor can also transmit and the first sensor can receive a pulse in a second direction opposite the first direction to provide a second measurement of the time of flight, allowing characteristics of the gas flow, such as a flow rate or velocity, to be determined. In another acoustic sensing topology, acoustic pulses transmitted by an acoustic transmitter, such as an ultrasonic transducer, can be received by acoustic receivers, such as microphones. More details of an acoustic flow rate sensor are described in International Patent No. WO2017095241A3, which is incorporated by reference herein in its entirety. The acoustic pulses can be transmitted along the flow path of the gases, thereby allowing the acoustic sensors to be used to measure a flow rate or velocity of the gases.

Readings from both the first and second types of sensors can be combined to determine a more accurate flow measurement. For example, a previously determined flow rate and one or more outputs from one of the types of sensor can be used to determine a predicted current flow rate. The predicted current flow rate can then be updated using one or more outputs from the other one of the first and second types of sensor, in order to calculate a final flow rate.

The respiratory system may be configured to deliver high flow therapy or Bubble CPAP therapy.

The respiratory device may be changeable between a high flow therapy mode and a Bubble CPAP therapy mode.

In the high flow therapy mode the respiratory device is configured to provide high flow therapy In the Bubble CPAP therapy mode the respiratory device is configured to provide bubble CPAP therapy.

The high flow therapy is nasal high flow therapy.

In the high flow therapy mode the system comprises an unsealed patient interface coupled to the inspiratory conduit 121.

The unsealed patient interface may be a nasal cannula.

In use, the nasal cannula is positioned on the user's face to provide gases to the nares of the user.

In the Bubble CPAP therapy mode the system comprises a sealed patient interface coupled to the inspiratory conduit 121, an expiratory conduit 130 coupled to the sealed patient interface.

The expiratory conduit 130 is coupled to a pressure regulator to regulate pressure within the patient interface and/or the patient's airways.

As described in more detail above, the pressure regulator comprises a chamber with a column of water and the expiratory conduit 130 being submerged into the column of water. The pressure provided to the user being defined or being set by the depth the submersion of the expiratory conduit 130 within the column of water.

The inspiratory conduit 121 may be common between the high flow therapy mode and the bubble CPAP therapy mode.

The same inspiratory conduit being useable for both modes reduces the number of components that are required to be interchanged when changing mode.

Further this common inspiratory conduit allows the same respiratory device comprising a blower and humidifier integrated into a housing to be used for both bubble CPAP mode and high flow mode. Further the integrated humidifier and blower in a common housing makes it simple to transition between bubble CPAP and high flow modes since a single device can be used, rather than unique set ups of several components as required in prior art systems.

The present system provides a single respiratory device that can be used to deliver both bubble CPAP therapy and high flow therapy, while only the interface requiring changes. There are no changes in components on the gases supply side i.e. no changes in the gases supply components since a common respiratory device can be used to deliver humidified gases.

Figure 7:
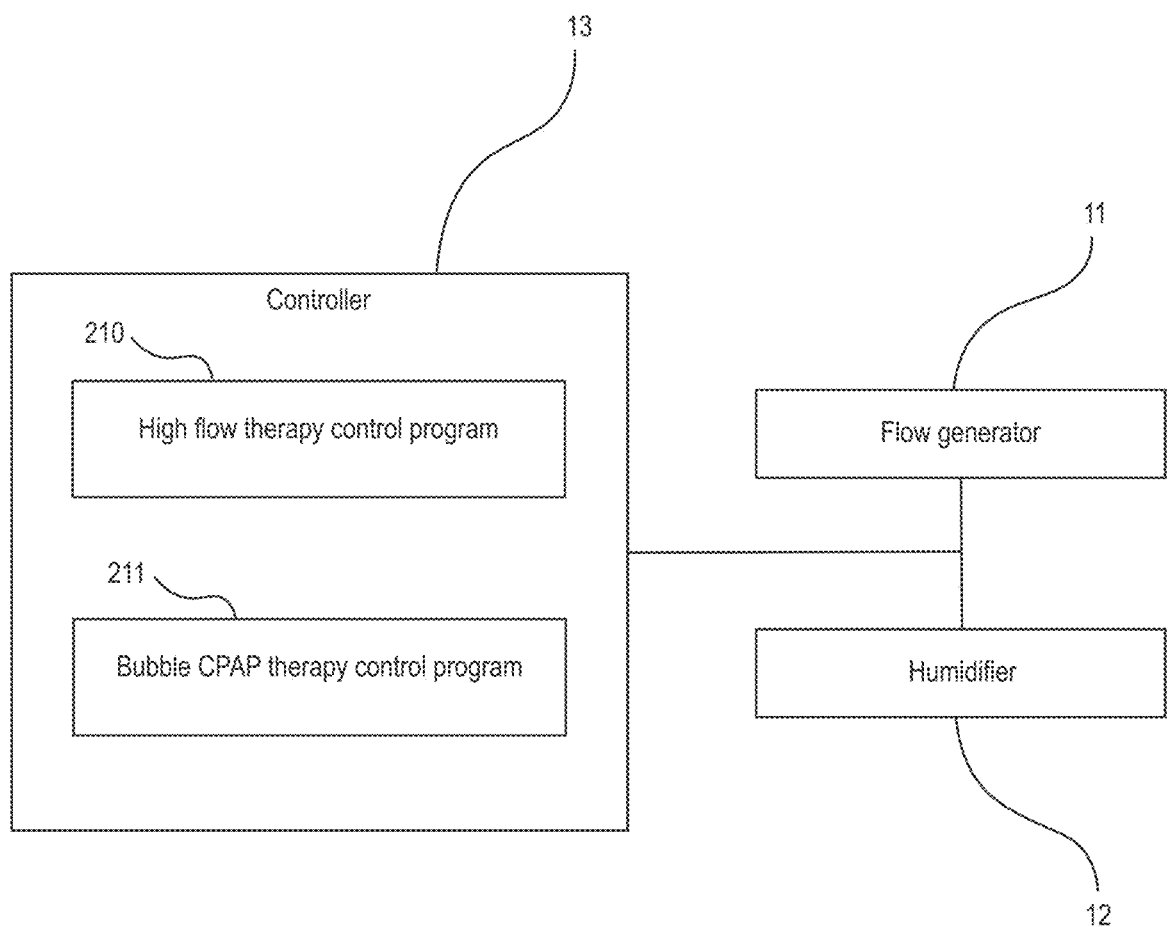
FIG. 7 illustrates a respiratory apparatus having a high flow therapy controller program, and a bubble CPAP therapy controller program.

As shown in FIG. 7, the controller 13 may comprise a high flow therapy control program 210 associated with the high flow therapy mode.

As shown in FIG. 7, the controller 13 may comprise a bubble CPAP therapy control program 211 associated with the bubble CPAP therapy mode.

In some embodiments, the high flow therapy mode may have a high flow therapy controller. Optionally the high flow therapy controller may be configured to run the high flow therapy control program 210.

In some embodiments, the bubble CPAP therapy mode may have a bubble CPAP therapy controller. Optionally the bubble CPAP therapy controller may be configured to run the bubble CPAP therapy control program 211.

The controller 13 is configured to select and apply the program 210, 211 that corresponds to the selected mode of operation.

Each of the high flow therapy control program 210, and the bubble CPAP therapy control program 211 defines corresponding operating parameters.

In some configurations, operating parameters may comprise one or more motor speed or pressure limits (for example a pressure cap), as described in more detail below.

Operating parameters may comprise one or more alarm conditions.

One or more alarm conditions may comprise a lack of bubbling in the bubble CPAP therapy mode.

In some embodiments, an alarm may be activated when lack of bubbling is detected for more than a threshold period of time.

Operating parameters may define a humidity level.

Operating parameters may one or more temperature or dew point set points to control the humidifier.

The humidity level provided during the high flow mode may be greater than the humidity level provided during bubble CPAP therapy mode.

The operating parameters may also define a flow limit corresponding to each mode.

The controller may be configured to detect bubbling of the bubbler, and wherein if bubbling is detected the controller selects the bubble CPAP therapy mode.

The controller may select the bubble CPAP therapy mode once bubbling has be detected for a predetermined amount of time.

The controller may present the user with a message to consider changing the mode to the bubble CPAP therapy mode once bubbling has be detected (optionally for a predetermined amount of time.)

The controller may automatically switch mode to the bubble CPAP therapy mode if a bubbler is detected by bubbling.

A user may select the high flow therapy mode, or the bubble CPAP therapy mode (optionally via a user interface).

The detection of bubbling may be that as described elsewhere in the specification.

Controlling $FdO_2$

As described above, the flow generator can be used as an oxygen and/or other breathable gas mixer. The flow generator that draws in ambient air can mix the air with oxygen from an oxygen source. This oxygen source can be from a high pressure source or a low pressure source.

When receiving oxygen from low pressure source, which may include an oxygen canister or tank, an oxygen wall source, or an oxygen concentrator, the respiratory device can receive a constant flow rate of oxygen. This oxygen can then be mixed with ambient air. The fraction of oxygen in the gas delivered to the patient ($FdO_2$) can be dependent on the set flow rate of oxygen from the low pressure source, and the total flow rate that the device generates. The device can measure $FdO_2$ and display it on the display.

When receiving oxygen from a high pressure source, which may include an oxygen canister or tank, an oxygen wall source, or an oxygen concentrator, the device can control the flow rate of oxygen by controlling the valve to the oxygen inlet port described herein. The $FdO_2$ can be dependent on the flow rate of oxygen through the valve (which can be further dependent on the state of the valve opening), and on the total flow rate that the device generates. A user, such as the clinician, can set a target $FdO_2$ on a user interface of the display, with the device then controlling the valve opening based on the target $FdO_2$ and measured $FdO_2$ in order to achieve the desired fraction of oxygen. Oxygen concentration can be measured by a variety of sensors, such as using the ultrasonic sensors described above. More details of example methods of measuring the oxygen concentration are described in International Patent No. WO2013151447A1, the entirety of which is incorporated herein by reference.

Controlling Flow Rate

As described above, bubble CPAP typically involves delivering a constant flow of gas to the patient.

In some configurations, blower and/or motor parameters may be controlled by flow generator to maintain the flow rate at a desired level.

For example the flow generator (or for example the controller) may control one or more of the motor speed, motor current, and/or motor voltage to a target motor speed, a target motor current, and/or a target motor voltage.

In some configurations, the respiratory device examples disclosed herein can measure the flow rate of gas, and control the motor speed of the flow generator based at least in part on the flow rate measurement in order to maintain a constant flow rate at a desired level.

The flow generator may for example control the motor speed of the motor to a target motor speed. The motor speed can correspond to a desired flow rate i.e. target flow rate. In one example motor speed is a control parameter because the controller may be able to achieve faster response since feedback from motor speed can be quickly read by the controller as compared to feedback from a sensor e.g. flow sensor downstream of the blower. Alternatively, the controller may use the flow reading from the flow sensor to control the motor.

The controller controls the blower to a target motor speed or a target flow or both. The controller preferably provides control signals to control i.e. vary the current or voltage or power provided to the motor of the blower in order achieve the target motor speed or target flow rate.

As a further alternative the controller may use a combination of motor speed and flow rate to control the motor. In this example, the controller may use feedback from the motor speed reading and the flow reading from a flow sensor to control the motor to achieve a target motor speed and/or a target flow rate.

Measuring the flow rate can be done by using one or more flow rate sensors. As described above, examples of sensors that can measure a flow rate of gas can include ultrasonic sensors and heated thermistors. Ultrasonic sensors can provide a faster signal, but are generally less accurate than heated thermistors. Heated thermistors can provide a more accurate signal, but may not respond to small quick changes in the flow. In nasal high flow systems described herein, the flow signal of the flow sensor needs to be filtered before being used to control the flow generator. This is because a patient receiving nasal high flow may cause fluctuations in the flow by coughing, talking, changing the cannula's positioning, etc. In this case, it can be desirable that the device does not make sudden changes to the motor speed based on these events.

However, when delivering bubble CPAP, these patient-caused fluctuations in the flow are less common. Therefore, the control of the flow rate can be designed to be more responsive to account for small leaks in the system, partial blockages, and/or dynamic changes in the patient's respiratory demand. The flow rate control can be done by using a shorter filter than in the nasal high flow therapy on the flow rate measurement. Additionally, and/or alternatively, the controller can use the flow rate measured by the ultrasonic sensors to provide a much faster signal. Additionally, and/or alternatively, the controller can use a combination of flow rates measured by the ultrasonic sensors and the heated thermistor. The controller can use the ultrasonic sensors to detect higher frequency changes in the flow rate, and use the heated thermistor to compensate for the lower accuracy measurements made by the ultrasonic sensors, which may be less accurate than when measured by the heated thermistor. The controller can also use other types of sensor(s) for measuring flow rate and/or pressure. The pressure and/or flow rate sensor can include a single sensor.

Once the system controller receives flow signals from the one or more flow rate sensors disclosed herein, the controller can measure the flow rate from the flow signals. The system controller can determine a difference between a target flow rate and the measured flow rate. The differences can be input into a PID controller. The PID controller can output a command to change to the motor speed of the flow generator based on the inputs. In one example the PID controller may output a current or voltage or power to the motor in order to control the motor speed.

The control of the flow rate can also be based on pressure measurements. In a conventional bubble CPAP system, a pressure relief valve is placed between the flow source and the patient. The pressure relief valve is a passive valve that can open at a set pressure in order to vent off a portion of the gas flow, thereby limiting the pressure of the gas delivered to the patient.

By using a flow generator to provide the flow of gas, the pressure limit can be implemented on the motor speed of the flow generator via software. The high flow system described herein may not include an additional valve for venting of excess flow. The control of the motor speed can provide a more accurate control of the pressure than the venting of the gas through the pressure relief valve, as the motor speed of the flow generator can be directly controlled based on the measured pressure. The use of a respiratory system (i.e. a respiratory device) with a flow generator, as described herein, does not require a pressure relief valve since the flow generator can be controlled to reduce the motor speed to generate less pressure if a pressure limit is reached. The system is simplified and requires less components since the system does not require a pressure relief valve and also does not require a gases source.

Figure 5:
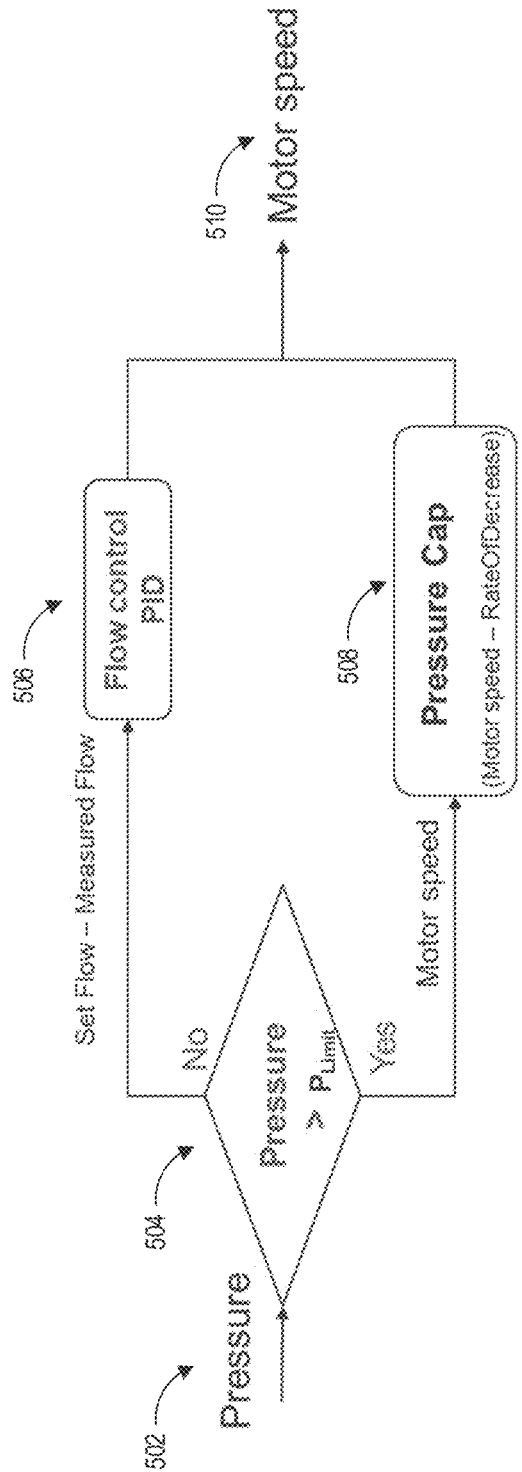
FIG. 5 illustrates an example block diagram for motor control in a respiratory apparatus with a flow generator providing bubble CPAP.

FIG. 5 illustrates an example block diagram of the motor control by the device controller. The device controller can receive inputs 502 from one or more pressure sensors. The controller can measure the pressure delivered to the patient from the pressure sensor inputs. The pressure sensor can be located downstream of the flow generator. For example, the pressure sensor can be located at or near the patient interface. The pressure sensor can also be located directly after the flow generator. The pressure delivered to the patient can be determined by taking the difference between the ambient pressure and the absolute pressure downstream of the flow generator. The pressure delivered to the patient can be estimated by measuring the pressure in the main device housing downstream of the flow generator and calculating the pressure drop along the inspiratory conduit. The pressure sensor(s) can also be located at other locations in the gases flow. The pressure measurements can also optionally be calculated, at least in part, based on flow rate. The pressure sensor can include a gauge pressure sensor, or alternatively two absolute pressure sensors. The gauge pressure sensor can directly measure a difference between the absolute pressure downstream of the flow generator and the ambient pressure. In systems having two absolute pressure sensors, one sensor can be located downstream of the flow generator to measure the absolute pressure downstream of the flow generator and the other sensor can be located in a different location to measure the ambient pressure. The controller can determine the pressure delivered to the patient by determining the differences between the pressure measurements made by the two absolute pressure sensors.

At decision logic 504, the controller can compare the measured pressure (as for example described above) with a predetermined pressure limit. The pressure limit can be set above the maximum pressure at which the bubbler can be set. In some configurations, the bubbler can be set at a maximum pressure of about 10 cmH2O, and the pressure limit for pressure control can be set at, for example, about 12 cmH2O, about 13 cmH2O, about 14 cmH2O, about 15 cmH2O, about 16 cmH2O, about 17 cmH2O, or about 18 cmH2O.

The pressure limit may be based on ambient pressure.

The relationship between the pressure limit may be linear, or non-linear.

The pressure limit may be based on a fixed amount or percentage above the ambient pressure.

The pressure limit being based on ambient pressure allows for compensation of ambient pressure. This may be of importance in a bubble CPAP system as the maximum pressure of the bubbler will be effected by ambient pressure, and so the effect of ambient pressure may be incorporated in the determination of the pressure limit.

In some embodiments, the pressure limit may be based on a predetermined ambient pressure (for example a preset non-measured ambient pressure).

The pressure limit may be set by the user.

If the measured pressure is below the limit, the controller can adjust the motor speed based on the output of a flow-based PID controller 506 described herein. The controller can input a difference between a target or set flow rate (such as set by a user) and the measured flow rate into the PID controller. The controller can output the motor speed determined by the PID controller, which is configured to maintain the target flow rate, as the output 510.

If the measured pressure is above the pressure limit, the controller can implement a pressure cap algorithm 508. The pressure cap algorithm 508 can decrease the target motor speed by a set amount, a set rate of decrease, a variable rate of decrease, or using a pressure-based PID control. The controller can output the reduced motor speed as the output 510 of the control. The target motor speed is decreased at each iteration of the motor control as shown in FIG. 5 until the measured pressure is below the pressure limit. The target motor speed can be reduced at a constant rate or variable rate.

In some embodiments, the pressure cap algorithm 508 can decrease the target motor speed proportional to the amount the measured pressure exceeds the pressure limit (for example as part of proportional control).

In some embodiments, the pressure cap algorithm 508 can decrease the target motor speed to decrease the measured pressure to below the pressure limit within a predetermined time period. For example the pressure cap algorithm 508 may decrease the target motor speed such that the measured pressure is below the pressure limit within about 2 to about 20 seconds, or within about seconds 5 to about 15 seconds, or within about 10 seconds.

In some embodiments, a set rate of decrease of the target motor speed may be set high enough so as to reduce the measured pressure below the pressure within the predetermined time.

Additionally, and/or alternatively, the device can output a visual, audible, and/or tactile alarm when the measured pressure exceeds the threshold.

In some configurations, the device can prevent the motor from exceeding a set speed in order to further prevent exceedingly high pressures from being delivered to the patient. The motor speed limit can act as a failsafe measure in situations in which the one or more sensors output false pressure measurements and/or are otherwise faulty. That is, two checks can be available to prevent the pressure of the gases flow from exceeding a predetermined maximum value. One check can be the pressure cap. The other check can be the maximum motor speed limit in case the pressure sensor readings are erroneous.

In some embodiments, the motor speed limit may be variable.

The motor speed limit can be based on ambient pressure. This may allow for example the motor speed limit to for example account for the altitude of the device.

The relationship between the motor speed limit and ambient pressure may be linear or non-linear.

In some embodiments the motor speed limit may be a first motor speed (for example 10,000 RPM) when the ambient pressure is a first ambient pressure (for example about 101 kPa (i.e. approximately sea level)).

In some embodiments the motor speed limit may be a second motor speed (for example about 15,000 RPM) when the ambient pressure is a second ambient pressure (for example about 79.5 kPa (i.e. approximately 2000 meters above sea level), or for example about 70.1 kPa (i.e. approximately 3000 meters above sea level).

The motor speed limit may vary between the first and second motor speeds between the first and second ambient pressures.

In some embodiments, the motor speed limit may further be based on an ambient temperature.

Detection of Bubbling

The flow generator of the high flow device can also be configured to detect the presence of bubbling in the bubbler. Bubbling can be useful in indicating that the system is operating correctly. For example, a temporary lack of bubbling can indicate that the peak inspiratory flow of the patient is exceeding the flow rate delivered by the device at that moment. Additionally, a prolonged lack of bubbling can indicate that there is a leak in the gas pathway, such as in the breathing circuit.

Bubbling can be detected by detecting the presence of oscillations in the pressure and/or flow. In respiratory systems in which the flow rate is being controlled by the device controller, the controller can use the pressure signal inputs, such as from the pressure sensors disclosed herein, to determine the presence of bubbling.

Figure 6:
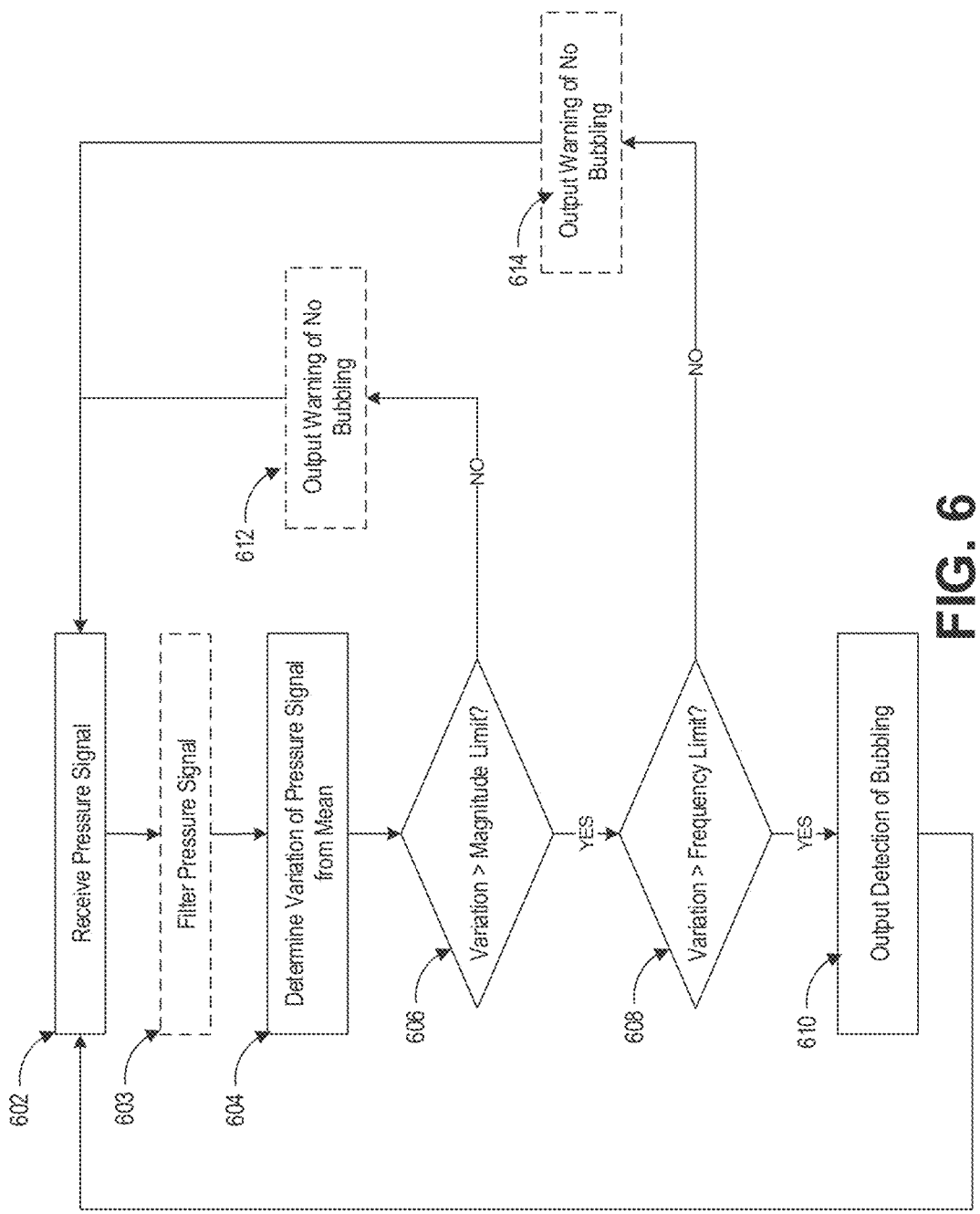
FIG. 6 illustrates an example flow chart for detecting bubbling when providing bubble CPAP.

FIG. 6 illustrates an example flow chart for determining whether bubbling can be detected. Although a pressure signal is used as an example in FIG. 6, the flow chart can also be applied to a flow signal, and/or to a combination of a pressure signal and a flow signal. At step 602, the controller can receive a pressure signal from the pressure sensor. At step 603, the pressure signal can be optionally filtered so that the amplitude measured is the amplitude of the measured pressure signal. At step 604, the controller can determine a variation of the pressure signal from a mean value of the pressure of the gas flow delivered to the patient (for example, measured by the one or more pressure sensors disclosed herein). At steps 606 and 608, the controller can determine whether oscillation is present in the pressure signal. Oscillation is present if the variation exceeds a specific magnitude 606, as well as above a specific frequency 608. For example, the pressure signal can be filtered using a high pass filter with a cut off frequency at about 5 Hz, or a band pass filter with cutoff frequencies at about 5 Hz and about 20 Hz. The specific magnitude (for example, when measured peak-to-peak) can be about 0.25 cmH2O. The threshold magnitude can be a single threshold value, or can vary depending on the set flow rate or pressure. If such an oscillation is present, the controller can output an indication that bubbling is deemed to be occurring at step 610. In the example provided herein, if oscillations are present in the filtered signal of a magnitude (for example, when measured peak-to-peak) above about 0.25 cmH2O, the controller can determine that bubbling has been detected. The controller can determine that bubbling cannot be determined if the magnitude does not exceed about 0.25 cmH2O. Alternatively, the controller can analyze the power spectrum at the frequency domain. If there is enough power in the frequency band, the controller can determine that bubbling is detected. Otherwise, the controller can determine that no bubbling is detected. The controller can then return to step 602. At step 606, if the variation does not exceed the magnitude limit, and/or at step 608, if the variation does not exceed the frequency limit, the controller can return to step 602 to repeat the bubbling detection process. The controller can optionally output a visual, audio, and/or tactile alarm that bubbling is absent at steps 612, 614.

The controller can also optionally monitor a duration for which bubbling is deemed to be absent. If bubbling is not detected for a predetermined duration, such as about 5 seconds, about 10 seconds, about 15 seconds, about 20 seconds, or longer, the controller can optionally output a message prompting a user to check for leaks in the gas pathway of the respiratory system.

Terminology

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations, one or more features from a claimed combination can, in some cases, be excised from the combination, and the combination may be claimed as a sub-combination or variation of a sub-combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

Any methods disclosed herein need not be performed in the order recited. The methods disclosed herein include certain actions taken by a practitioner; however, they can also include any third-party instruction of those actions, either expressly or by implication. For example, actions such as "controlling a motor speed" include "instructing controlling of a motor speed."

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, and/or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state. In some embodiments, the computer system may be a cloud-based computing system whose processing resources are shared by multiple distinct business entities or other users.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A respiratory system which is programmed to deliver both a high flow therapy and a bubble CPAP therapy, wherein the respiratory system comprises:
   a flow generator;
   a humidifier in fluid communication with the flow generator;
   an inspiratory conduit in fluid communication with the humidifier; and
   a controller configured to control the flow generator to provide the high flow therapy and the bubble CPAP therapy, the controller changeable between the high flow therapy and the bubble CPAP therapy;
   wherein the controller is further configured to detect bubbling of a bubbler by monitoring a variation in a flow parameter signal, and wherein in response to the controller detecting bubbling, the controller is configured to output an indication that bubbling is detected or select or switch to the bubble CPAP therapy.

2. The respiratory system of claim 1, wherein the controller is configured to provide is nasal high flow therapy.

3. The respiratory system of claim 1, further comprising a non-sealing patient interface coupled to the inspiratory conduit for use when high flow therapy is provided.

4. The respiratory system of claim 3, wherein the non-sealing patient interface is a nasal cannula.

5. The respiratory system of claim 1, further comprising:
   a sealed patient interface coupled to the inspiratory conduit; and
   an expiratory conduit coupled to the sealed patient interface for use when bubble CPAP therapy is provided;
   wherein the expiratory conduit is coupled to a pressure regulator to regulate pressure within the sealed patient interface and/or a patient's airways, wherein the pressure regulator comprises a chamber with a column of water, the expiratory conduit being submerged into the column of water at a depth, and wherein the pressure provided to a user is defined or is set by the depth of submersion of the expiratory conduit within the column of water.

6. The respiratory system of claim 1, further comprising a housing, wherein the flow generator and humidifier are integrated into the housing.

7. The respiratory system of claim 1, wherein the inspiratory conduit is configured to be used during the high flow therapy and the bubble CPAP therapy.

8. The respiratory system of claim 1, wherein the controller comprises:
   a high flow therapy control program associated with the high flow therapy; and
   a bubble CPAP therapy control program associated with the bubble CPAP therapy;
   wherein the controller is further configured to:
   select and apply the high flow therapy control program when the high flow therapy is selected; and
   select and apply the bubble CPAP therapy control program when the bubble CPAP therapy is selected.

9. The respiratory system of claim 8, wherein the high flow therapy control program and/or the bubble CPAP therapy control program define operating parameters.

10. The respiratory system of claim 9, wherein the operating parameters comprise at least one of:
    one or more motor speed or pressure limits,
    one or more alarm conditions,
    one or more temperature set points, or
    one or more flow limits.

11. The respiratory system of claim 9, wherein the operating parameters comprises one or more humidity parameters defining a humidity level.

12. The respiratory system of claim 11, wherein a humidity level to be provided during the high flow therapy is greater than the humidity level to be provided during the bubble CPAP therapy.

13. The respiratory system of claim 1, wherein the controller is configured to automatically switch therapies when bubbling of the bubbler is detected.

14. The respiratory system of claim 1, wherein the flow parameter signal comprises a flow signal, a pressure signal, or a combination thereof.

15. The respiratory system of claim 1, wherein the variation in the flow parameter signal is a variation of a flow parameter signal amplitude from a threshold value or wherein the variation in the flow parameter signal is analyzed in a frequency domain.

16. The respiratory system of claim 1, wherein the controller providing one of the high flow therapy or the bubble CPAP therapy is a mode selection configured to be selectable by a user.

17. The respiratory system of claim 1, further comprising a high flow therapy mode kit, wherein the high flow therapy mode kit comprises: a non-sealing patient interface.

18. The respiratory system of claim 1, further comprising a bubble CPAP therapy mode kit, wherein the bubble CPAP therapy mode kit comprises: a sealing patient interface, an expiratory conduit, and/or a bubbler.

\* \* \* \* \*

UNITED STATES PATENT AND TRADEMARK OFFICE
CERTIFICATE OF CORRECTION

| | | |
|---|---|---|
| PATENT NO. | : 12,377,239 B2 | Page 1 of 1 |
| APPLICATION NO. | : 17/593353 | |
| DATED | : August 5, 2025 | |
| INVENTOR(S) | : Hsu et al. | |

It is certified that error appears in the above-identified patent and that said Letters Patent is hereby corrected as shown below:

In the Specification

In Column 2, Line 67, delete "a bubbler)" and insert --a bubbler).--.

In Column 11, Line 54, delete "that may by ambient" and insert --that may be ambient--.

In Column 18, Line 64, delete "flow therapy" and insert --flow therapy.--.

In the Claims

In Column 28, Claim 2, Line 18, delete "provide is nasal" and insert --provide nasal--.

Signed and Sealed this
Eighteenth Day of November, 2025

John A. Squires
*Director of the United States Patent and Trademark Office*